United States Patent
Bobgan et al.

(10) Patent No.: US 12,285,620 B2
(45) Date of Patent: Apr. 29, 2025

(54) IMD ENCLOSURE FORMED USING DIELECTRIC MATERIALS INCORPORATING FEEDTHRU(S)

(71) Applicant: Cardiac Pacemakers, Inc., St Paul, MN (US)

(72) Inventors: Jean M. Bobgan, Maple Grove, MN (US); James M. English, Cahir (IE); Keith R. Maile, New Brighton, MN (US); Ron A. Balczewski, Bloomington, MN (US)

(73) Assignee: Cardiac Pacemakers, Inc., St Paul (MN)

( * ) Notice: Subject to any disclaimer, the term of this patent is extended or adjusted under 35 U.S.C. 154(b) by 487 days.

(21) Appl. No.: 17/495,952

(22) Filed: Oct. 7, 2021

(65) Prior Publication Data

US 2022/0111218 A1    Apr. 14, 2022

Related U.S. Application Data

(60) Provisional application No. 63/089,926, filed on Oct. 9, 2020.

(51) Int. Cl.
*A61N 1/375* (2006.01)
*A61N 1/372* (2006.01)

(52) U.S. Cl.
CPC ....... *A61N 1/3754* (2013.01); *A61N 1/37229* (2013.01); *A61N 1/375* (2013.01); *A61N 1/3756* (2013.01)

(58) Field of Classification Search
None
See application file for complete search history.

(56) References Cited

U.S. PATENT DOCUMENTS

2010/0004711 A1    1/2010  Hahn
2010/0293774 A1*  11/2010  Haller ................ A61N 1/37512
                                                                29/428

(Continued)

FOREIGN PATENT DOCUMENTS

EP          2714191 A2    4/2014
WO      2012/161915 A2   11/2012

OTHER PUBLICATIONS

International Search Report and Written Opinion received for PCT Patent Application No. PCT/US2021/053885, mailed on Jan. 31, 2022, 12 pages.

*Primary Examiner* — Erica S Lee
(74) *Attorney, Agent, or Firm* — Faegre Drinker Biddle & Reath LLP

(57) ABSTRACT

Embodiments of the present disclosure relate to implantable medical device (IMD) enclosures. In an exemplary embodiment, an IMD comprises: a housing comprising an open end and a header defining a cavity and comprising at least one conduit through a wall of the header, wherein the header is formed from a non-conductive material. Further, the IMD comprises a coupling member comprising a flange, wherein the flange is configured to be received by the open end of the housing and wherein the flange and the open end of the housing at least partially overlap along an axial direction of the IMD when the flange is received by the open end. Additionally, the IMD comprises an electrode arranged on an outer surface of the header and a feedthrough coupled to the electrode and extending through the conduit of the header, wherein the feedthrough is configured to be coupled to internal circuitry housed within the IMD. Further, the IMD comprises a ring forming a hermetic seal between the coupling member and the header.

17 Claims, 8 Drawing Sheets

(56) References Cited

U.S. PATENT DOCUMENTS

| | | | |
|---|---|---|---|
| 2014/0133123 A1 | 5/2014 | Prasannakumar et al. | |
| 2016/0015564 A1* | 1/2016 | Pang | A61M 5/14276 |
| | | | 604/9 |
| 2016/0263384 A1* | 9/2016 | Stevenson | H01G 4/12 |
| 2017/0266451 A1* | 9/2017 | Lim | A61N 1/362 |
| 2017/0303411 A1 | 10/2017 | Bobgan et al. | |
| 2017/0303424 A1 | 10/2017 | Bobgan et al. | |
| 2018/0140852 A1* | 5/2018 | Linder | A61N 1/3787 |
| 2019/0232066 A1* | 8/2019 | Lim | A61N 1/3754 |
| 2020/0196960 A1* | 6/2020 | Kharam | A61B 5/352 |
| 2020/0397355 A1* | 12/2020 | Kuhn | A61B 5/1118 |
| 2020/0398042 A1* | 12/2020 | Tischendorf | A61N 1/3605 |
| 2021/0001130 A1* | 1/2021 | Wolf, II | A61N 1/3752 |
| 2021/0083370 A1* | 3/2021 | Landherr | H01Q 7/00 |
| 2021/0187291 A1* | 6/2021 | Iyer | B23K 26/21 |

\* cited by examiner

IMD ENCLOSURE FORMED USING DIELECTRIC MATERIALS INCORPORATING FEEDTHRU(S)

CROSS REFERENCE TO RELATED APPLICATION

This application claims priority to Provisional Application No. 63/089,926, filed Oct. 9, 2020, all of which are herein incorporated by reference in their entirety.

TECHNICAL FIELD

Embodiments of the present disclosure relate to medical devices for sensing physiological parameters and/or delivering therapy. More specifically, embodiments of the disclosure relate to implantable medical device enclosures formed using dielectric materials and incorporating feedthru(s) used to sense physiological parameters and/or deliver therapy.

BACKGROUND

Implantable medical devices (IMDs) may be configured to sense physiological parameters and/or provide therapy and may include one or more electrodes for performing aspects of these functions. IMDs may also include antennas for communicating with other devices. Conventionally, devices such as programmers and wands have been used to cause IMDs to take various actions such as for example, marking recordings of physiological parameters, initiating communications with other devices, and the like.

SUMMARY

Examples of implantable medical device enclosures formed using dielectric materials and incorporating feedthru(s) used to sense physiological parameters and/or deliver therapy include, but are not limited to, the following.

In an Example 1, implantable medical device (IMD), comprising: a housing comprising an open end; a header defining a cavity and comprising at least one conduit through a wall of the header, wherein the header is formed from a non-conductive material; a coupling member comprising a flange, wherein the flange is configured to be received by the open end of the housing and wherein the flange and the open end of the housing at least partially overlap along an axial direction of the IMD when the flange is received by the open end; an electrode arranged on an outer surface of the header; a feedthrough coupled to the electrode and extending through the conduit of the header, wherein the feedthrough is configured to be coupled to internal circuitry housed within the IMD; and a ring forming a hermetic seal between the coupling member and the header.

In an Example 2, the IMD of Example 1, further comprising an antenna positioned within the cavity of the header and pressed onto an internal surface of the header so that the internal surface of the header supports the antenna.

In an Example 3, the IMD of Example 2, wherein the antenna is positioned equidistant from a first side and a second side of the header, wherein the first side is opposite the second side.

In an Example 4, the IMD of Example 2, wherein the antenna is formed from gold.

In an Example 5, the IMD of any one of Examples 1-4, wherein the non-conductive material is zirconia or alumina.

In an Example 6, the IMD of any one of Examples 1-5, wherein the ring is formed from gold.

In an Example 7, the IMD of any one of Examples 1-6, further comprising at least one selected from the group of: a recharge coil, an optical window, and an optical sensor.

In an Example 8, the IMD of any one of Examples 1-7, further comprising a preform ring coupling the feedthrough to the electrode.

In an Example 9, the IMD of any one of Examples 1-8, wherein the coupling member is formed from titanium.

In an Example 10, a method of manufacturing an implantable medical device (IMD), comprising: injection molding or milling a header comprising a cavity, wherein the header is formed from a non-conductive material; forming a conduit through a wall of the header; inserting a feedthrough into the conduit, wherein the feedthrough is configured to be coupled to internal circuitry housed within the IMD; arranging an electrode on an outer surface of the header that contacts the feedthrough; coupling a housing to the header using a coupling member comprising a flange, wherein the flange is received by an open end of the housing and wherein the flange and the open end of the housing at least partially overlap along an axial direction of the IMD when the flange is received by the open end; and forming a hermetic seal at a junction between the coupling member and the header.

In an Example 11, the method of Example 10, further comprising positioning an antenna within the cavity of the header and pressing the antenna onto an internal surface of the header so that the internal surface of the header supports the antenna.

In an Example 12, the method of Example 11, wherein the antenna is positioned equidistant from a first side and a second side of the header.

In an Example 13, the method of Example 11, further comprising forming the antenna from gold.

In an Example 14, the method of any one of Examples 10-13, wherein arranging the electrode on the outer surface of the header comprises sputtering the electrode on the outer surface of the header.

In an Example 15, the method of any one of Examples 10-14, wherein arranging the electrode on the outer surface of the header comprises using photolithography to form the electrode on the outer surface of the header.

In an Example 16, an implantable medical device (IMD), comprising: a housing comprising an open end; a header defining a cavity and comprising at least one conduit through a wall of the header, wherein the header is formed from a non-conductive material; a coupling member comprising a flange, wherein the flange is configured to be received by the open end of the housing and wherein the flange and the open end of the housing at least partially overlap along an axial direction of the IMD when the flange is received by the open end; an electrode arranged on an outer surface of the header; a feedthrough coupled to the electrode and extending through the conduit of the header, wherein the feedthrough is configured to be coupled to internal circuitry housed within the IMD; and a ring forming a hermetic seal between the coupling member and the header.

In an Example 17, the IMD of Example 16, further comprising an antenna positioned within the cavity of the header and pressed onto an internal surface of the header so that the internal surface of the header supports the antenna.

In an Example 18, the IMD of Example 17, wherein the antenna is positioned equidistant from a first side and a second side of the header, wherein the first side is opposite the second side.

In an Example 19, the IMD of Example 17, wherein the antenna is formed from gold.

In an Example 20, the IMD of Example 16, wherein the non-conductive material is zirconia or alumina.

In an Example 21, the IMD of Example 16, wherein the ring is formed from gold.

In an Example 22, the IMD of Example 16, further comprising at least one selected from the group of: a recharge coil, an optical window, and an optical sensor.

In an Example 23, the IMD of Example 16, further comprising a preform ring coupling the feedthrough to the electrode.

In an Example 24, the IMD of Example 16, wherein the coupling member is formed from titanium.

In an Example 25, a method of manufacturing an implantable medical device (IMD), comprising: injection molding or milling a header comprising a cavity, wherein the header is formed from a non-conductive material; forming a conduit through a wall of the header; inserting a feedthrough into the conduit, wherein the feedthrough is configured to be coupled to internal circuitry housed within the IMD; arranging an electrode on an outer surface of the header that contacts the feedthrough; coupling a housing to the header using a coupling member comprising a flange, wherein the flange is received by an open end of the housing and wherein the flange and the open end of the housing at least partially overlap along an axial direction of the IMD when the flange is received by the open end; and forming a hermetic seal at a junction between the coupling member and the header.

In an Example 26, the method of Example 25, further comprising positioning an antenna within the cavity of the header and pressing the antenna onto an internal surface of the header so that the internal surface of the header supports the antenna.

In an Example 27, the method of Example 26, wherein the antenna is positioned equidistant from a first side and a second side of the header.

In an Example 28, the method of Example 26, further comprising forming the antenna from gold.

In an Example 29, the method of Example 25, wherein arranging the electrode on the outer surface of the header comprises sputtering the electrode on the outer surface of the header.

In an Example 30, the method of Example 25, wherein arranging the electrode on the outer surface of the header comprises using photolithography to form the electrode on the outer surface of the header.

In an Example 31, the method of Example 25, wherein arranging the electrode on the outer surface of the header comprises brazing the electrode on the outer surface of the electrode.

In an Example 32, the method of Example 25, wherein forming the hermetic seal at the junction between the coupling member and the header comprises brazing a ring to the junction between the coupling member and the header.

In an Example 33, the method of Example 25, wherein the non-conductive material is zirconia or alumina.

In an Example 34, the method of Example 25, further comprising forming the coupling member from titanium.

In an Example 35, an implantable medical device (IMD), comprising: a housing comprising an open end; a header defining a cavity, wherein the header is formed from a non-conductive material and wherein the header comprises a flange, wherein the flange is configured to be received by the open end of the housing and wherein the flange and the open end of the housing at least partially overlap along an axial direction of the IMD when the flange is received by the open end; an antenna positioned within the cavity of the housing and pressed onto an internal surface of the housing so that the internal surface of the housing supports the antenna; and a ring forming a hermetic seal at a junction between the coupling member and the header.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
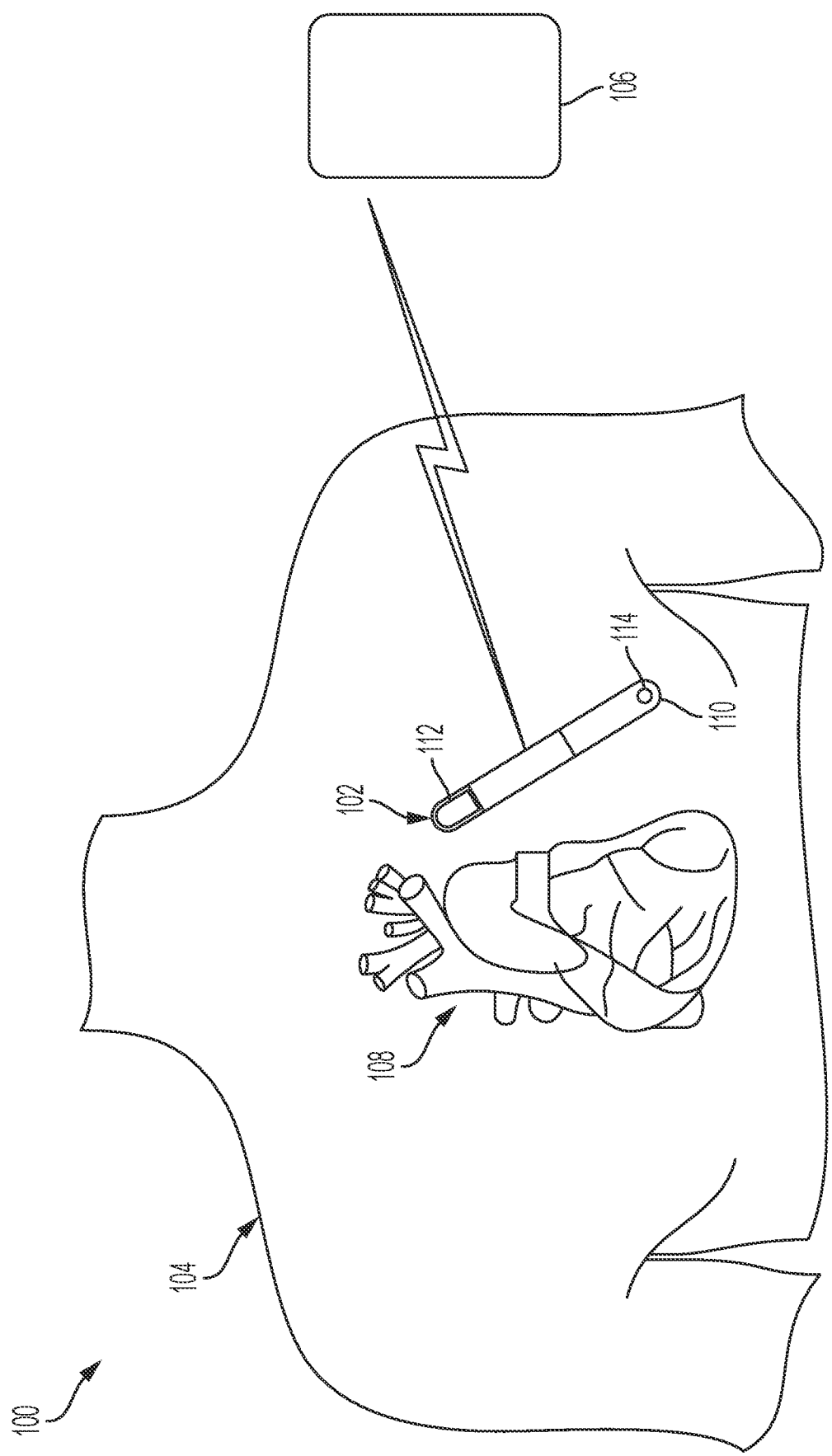
FIG. 1 is a schematic illustration of a system having an implantable medical device (IMD) and a receiving device, in accordance with embodiments of the disclosure.

While the disclosed subject matter is amenable to various modifications and alternative forms, specific embodiments have been shown by way of example in the drawings and are described in detail below. The intention, however, is not to limit the disclosed subject matter to the particular embodiments described. On the contrary, the disclosed subject matter is intended to cover all modifications, equivalents, and alternatives falling within the scope of the disclosed subject matter as defined by the appended claims.

Although the term "block" may be used herein to connote different elements illustratively employed, the term should not be interpreted as implying any requirement of, or particular order among or between, various steps disclosed herein unless and except when explicitly referring to the order of individual steps.

DETAILED DESCRIPTION

An implantable medical device (IMD) oftentimes have a header that is formed via overmolding, which can facilitate holding various components in place. This overmolding process can be costly with yield fallout and/or result in wasted space. Embodiments of the present disclosure improve upon these types of IMDs.

FIG. 1 is a schematic illustration of a system 100 including an implantable medical device (IMD) 102 implanted within a patient's body 104 and configured to communicate with a receiving device 106. In embodiments, the IMD 102 may be implanted subcutaneously within an implantation location or pocket in the patient's chest or abdomen and may be configured to monitor (e.g., sense and/or record) physiological parameters associated with the patient's heart 108. In embodiments, the IMD 102 may be an implantable cardiac monitor (ICM) (e.g., an implantable diagnostic monitor (IDM), an implantable loop recorder (ILR), etc.) configured to record physiological parameters such as, for example, one or more cardiac activation signals, heart sounds, blood pressure measurements, oxygen saturations, and/or the like. In embodiments, the IMD 102 may be configured to monitor physiological parameters that may include one or more signals indicative of a patient's physical activity level and/or metabolic level, such as an acceleration signal. In embodiments, the IMD 102 may be configured to monitor physiological parameters associated with one or more other organs, systems, and/or the like. The IMD 102 may be configured to sense and/or record at regular intervals, continuously, and/or in response to a detected event. In embodiments, such a detected event may be detected by one or more sensors of the IMD 102, another IMD (not shown), an external device (e.g., the receiving device 106), and/or the like. In addition, the IMD 102 may be configured to detect a variety of physiological signals that may be used in connection with various diagnostic, therapeutic, and/or monitoring implementations. For example, the IMD 102 may include sensors or circuitry for detecting respiratory system signals, cardiac system signals, and/or signals related to patient activity. In embodiments, the IMD 102 may be configured to sense intrathoracic impedance, from which various respiratory parameters may be derived, including, for example, respiratory tidal volume and minute ventilation. Sensors and associated circuitry may be incorporated in connection with the IMD 102 for detecting one or more body movement or body posture and/or position related signals. For example, accelerometers and/or GPS devices may be employed to detect patient activity, patient location, body orientation, and/or torso position.

For purposes of illustration, and not of limitation, various embodiments of devices that may be used to record physiological parameters in accordance with the present disclosure are described herein in the context of IMDs that may be implanted under the skin in the chest region of a patient.

As shown, the IMD 102 may include a housing 110. According to certain embodiments, the IMD 102 includes two electrodes 112 and 114. In certain embodiments, the IMD 102 may include any number of electrodes (and/or other types of sensors such as, e.g., thermometers, barometers, pressure sensors, optical sensors, motion sensors, and/or the like) in any number of various types of configurations, and the housing 110 may include any number of different shapes, sizes, and/or features. In embodiments, the IMD 102 may be configured to sense physiological parameters and record the physiological parameters. For example, the IMD 102 may be configured to activate (e.g., periodically, continuously, upon detection of an event, and/or the like), record a specified amount of data (e.g., physiological parameters) in a memory, and communicate that recorded data to a receiving device 106. In the case of an IDM, for example, the IMD 102 may activate, record cardiac signals for a certain period of time, deactivate, and activate to communicate the recorded signals to the receiving device 106.

In various embodiments, the receiving device 106 may be, for example, a programmer, controller, patient monitoring system, and/or the like. Although illustrated in FIG. 1 as an external device, the receiving device 106 may be and/or include an implantable device configured to communicate with the IMD 102 that may, for example, be a control device, another monitoring device, a pacemaker, an implantable defibrillator, a cardiac resynchronization therapy (CRT) device, and/or the like, and may be an implantable medical device known in the art or later developed, for providing therapy and/or diagnostic data about the patient and/or the IMD 102. In various embodiments, the IMD 102 may be a pacemaker, an implantable cardioverter defibrillator (ICD) device, or a cardiac resynchronization therapy (CRT) device. In various embodiments, the IMD 102 may include both defibrillation and pacing/CRT capabilities (e.g., a CRT-D device).

The system 100 may be used to implement coordinated patient measuring and/or monitoring, diagnosis, and/or therapy in accordance with embodiments of the disclosure. The system 100 may include, for example, one or more patient-internal medical devices, such as an IMD 102, and one or more patient-external medical devices, such as receiving device 106. In embodiments, the receiving device 106 may be configured to perform monitoring, and/or diagnosis and/or therapy functions external to the patient (i.e., not invasively implanted within the patient's body). The receiving device 106 may be positioned on the patient, near the patient, or in any location external to the patient.

In embodiments, the IMD 102 and the receiving device 106 may communicate through a wired or non-wired link. For example, the IMD 102 and the receiving device 106 may be coupled through a short-range radio link, such as Bluetooth, IEEE 802.11, and/or a proprietary wireless protocol. The communications link may facilitate uni-directional and/or bi-directional communication between the IMD 102 and the receiving device 106. Data and/or control signals may be transmitted between the IMD 102 and the receiving device 106 to coordinate the functions of the IMD 102 and/or the receiving device 106. In embodiments, patient data may be downloaded from one or more of the IMD 102 and the receiving device 106 periodically or on command. The physician and/or the patient may communicate with the IMD 102 and the receiving device 106, for example, to acquire patient data or to initiate, terminate, or modify recording and/or therapy.

The illustrative system 100 shown in FIG. 1 is not intended to suggest any limitation as to the scope of use or functionality of embodiments of the subject matter disclosed throughout this disclosure. Neither should the illustrative system 100 be interpreted as having any dependency or requirement related to any single component or combination of components illustrated in FIG. 1. For example, in embodiments, the illustrative system 100 may include additional components. Additionally, any one or more of the components depicted in FIG. 1 can be, in embodiments, integrated with various ones of the other components depicted therein (and/or components not illustrated). Any number of other components or combinations of components can be integrated with the illustrative system 100 depicted in FIG. 1, all of which are considered to be within the ambit of this disclosure.

Figure 2:
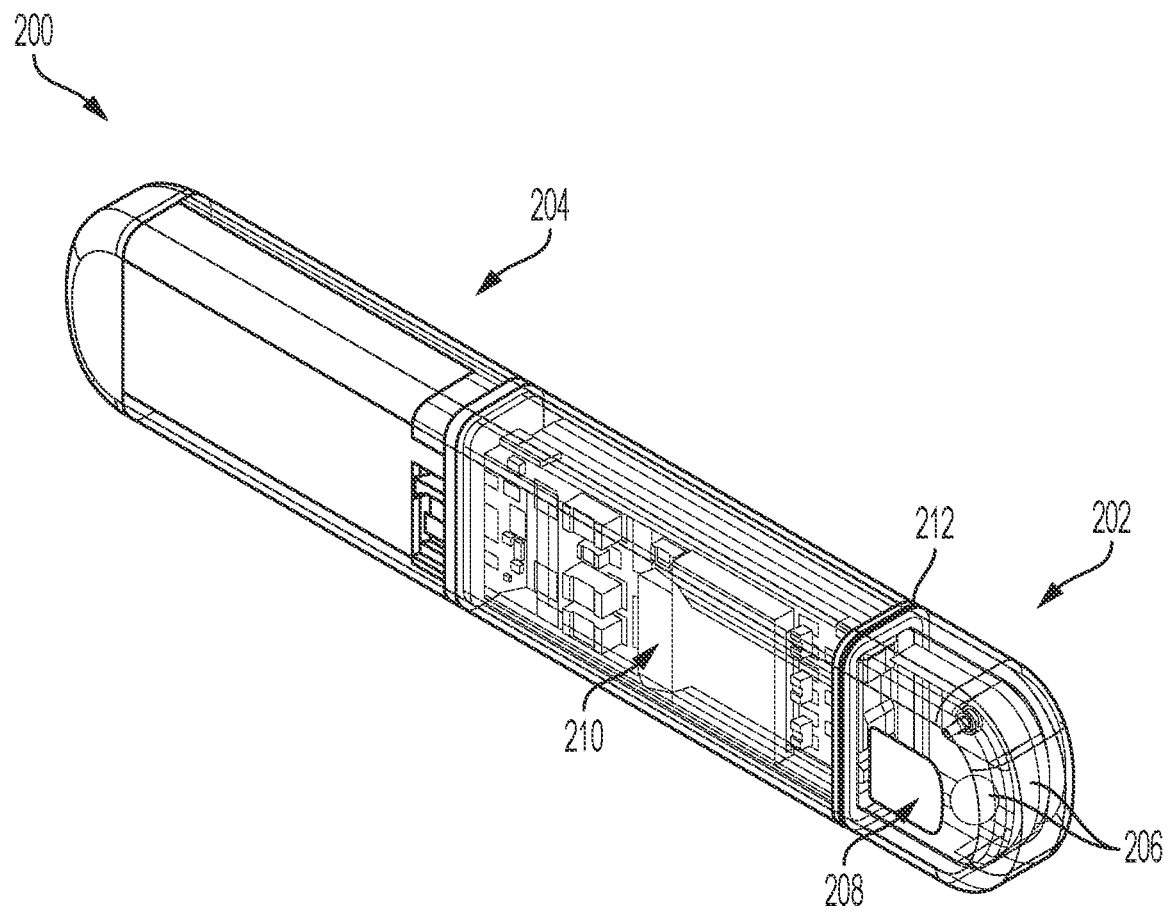
FIG. 2 is a perspective view of an IMD, in accordance with embodiments of the disclosure.

FIG. 2 is a perspective view of an IMD 200, in accordance with embodiments of the present disclosure. According to certain embodiments, the IMD 200 may be, or may be similar to, the IMD 102 depicted in FIG. 1.

As shown, the IMD 200 may include a header 202 arranged at or near an end portion of the housing 204. In certain embodiments, the header 202 is formed from a non-conductive and/or dielectric material. In certain instances, a non-conductive and/or dielectric material may include materials having an electrical resistivity greater than $10^5$ Ω·m at 20° C. Examples of non-conductive materials include, but are not limited to, bio-ceramics, such as yttria, zirconia, sapphire, alumina, and/or the like.

Figure 4:
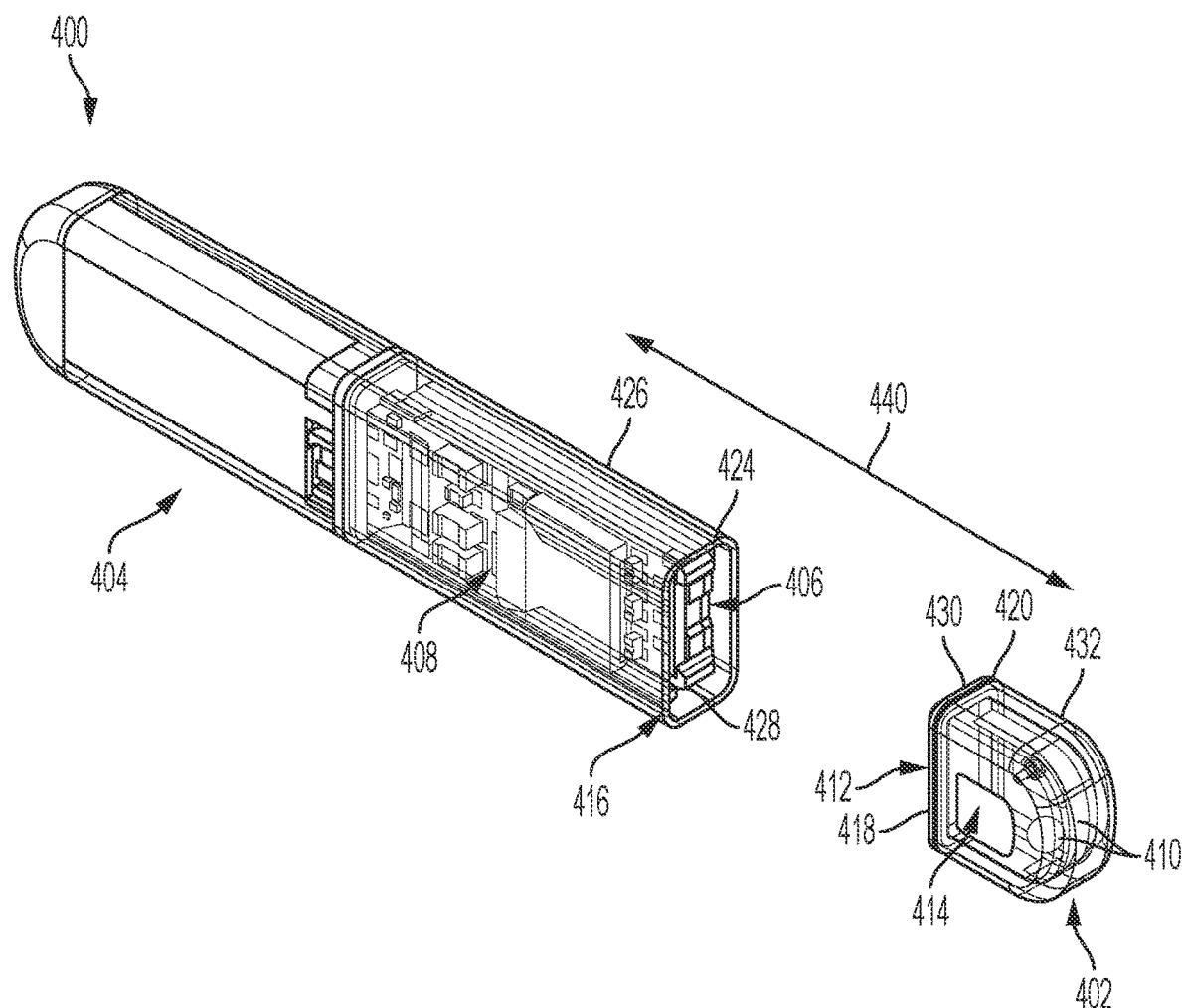
FIG. 4 is a perspective view an IMD with a header of the IMD separated from a housing of the IMD, in accordance with embodiments of the disclosure.
Figure 5:
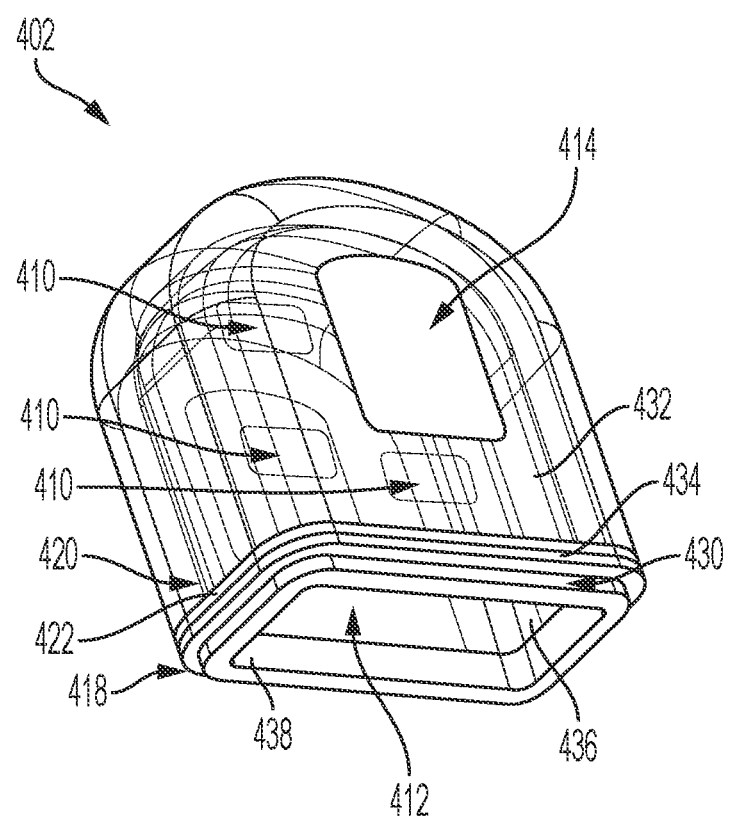
FIG. 5 is a perspective view of a header of an IMD, in accordance with embodiments of the disclosure.
Figure 6:
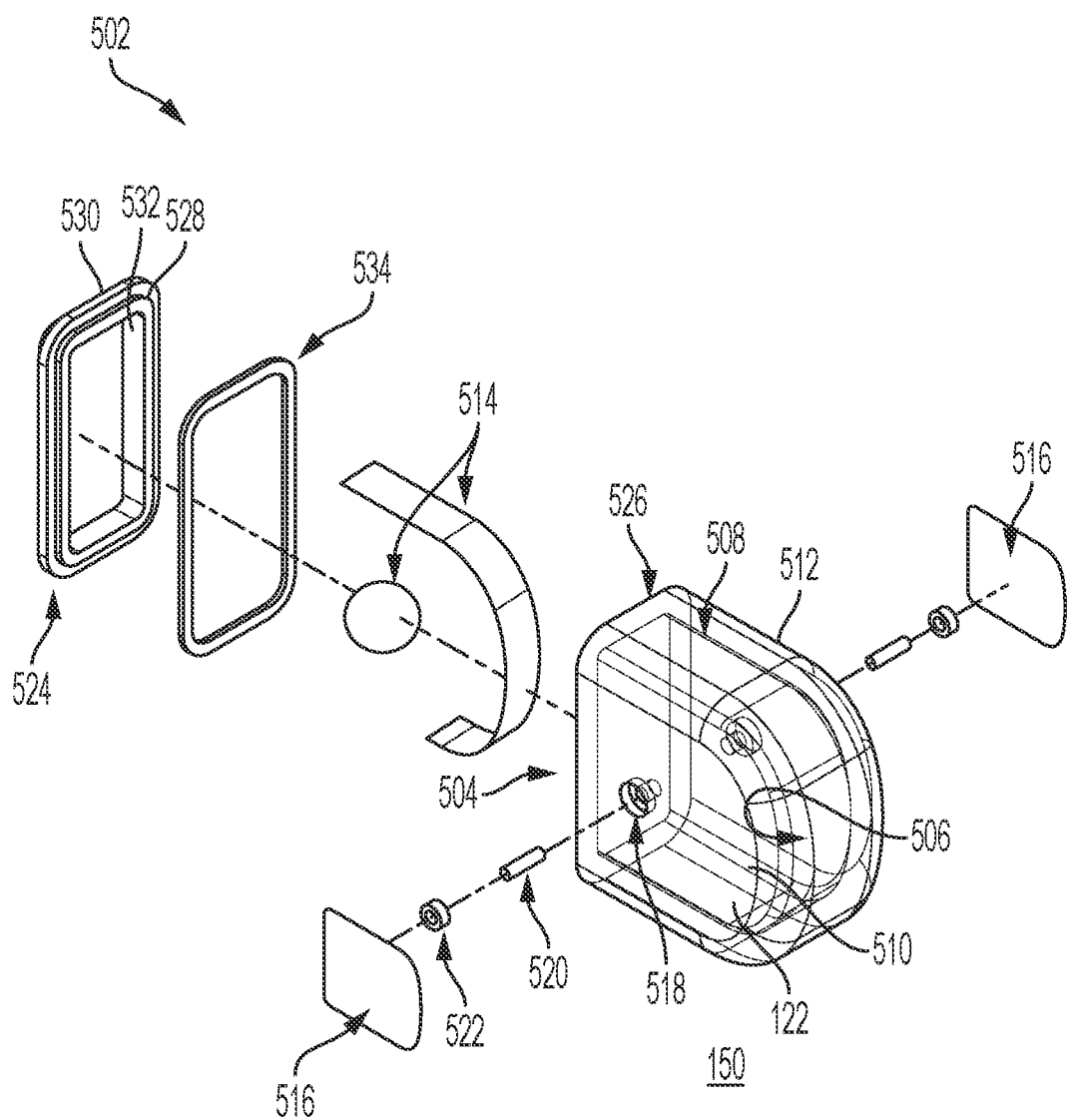
FIG. 6 is an exploded view of a header of an IMD, in accordance with embodiments of the disclosure.

In certain embodiments, the header 202 defines a cavity (see, e.g., the cavity 412 of FIGS. 4-5 and cavity 504 in FIG. 6). In some instances, the header 202 can be formed by, for example, injection molding, 3-D printing, machining (e.g., milling), sintering, and/or the like so the header 202 defines a cavity. In comparison, when a header is formed using an overmolding process, there is no cavity formed within the header. As such, headers formed using an overmolding process can result in wasted header space. Moreover, when a header is formed using an overmolding process, there can be yield fallout, resulting in additional costs associated with manufacturing the header. As such, the header 202 provides advantages over headers formed using an overmolding process.

According to some examples, one or more components 206 can be arranged within the cavity of the header 202. In certain instances, the one or more components 206 can be configured to and/or facilitate sensing physiological parameters, delivering therapy, and/or transmitting/receiving data. Examples of one or more components 206 include, but are not limited to, sensors, antennas, recharge coils, optical windows, electrical traces/connections, and/or the like. As explained in more detail below, the one or more components 206 arranged within the cavity of the header 202 may be supported by an internal surface of the cavity of the header 202. As mentioned above, due to the header 202 having a cavity, more space is available within the header 202 for components to be arranged therein.

According to certain embodiments, one or more electrodes 208 can be arranged on an outer surface of the header 202. In certain instances, the one or more electrodes 208 can be configured to and/or facilitate sensing physiological parameters and/or delivering therapy. In embodiments, the electrodes 208 can be coupled to one or more components 206 arranged within the header 202 through a conduit (illustrated in FIG. 6 below) in the header 202. In some examples, the one or more electrodes 208 can be sputtered onto a surface (e.g., an outer surface) of the header 202. In certain instances, the one or more electrodes 208 can be arranged onto a surface (e.g., an outer surface) of the header 202 using photolithography.

Additionally, or alternatively, the one or more components 206 and/or the one or more electrodes 208 can be coupled to internal components 210 arranged within the housing 204 of the IMD 200. According to certain embodiments, the internal components 210 may be used to control the one or more components 206 and/or the one or more electrodes 208.

According to certain embodiments, the header 202 can be coupled to and/or joined to the housing 204 via a coupling member 212 to form a hermetically sealed package. In certain examples, the coupling member 212 can be a metallic ring (e.g., titanium) that abuts, fits onto, and/or inserted into an open end of the header 202. In some examples, the coupling member 212 can be attached to the header 202 via brazing. And, the coupling member 212 can also be attached to the housing 204 via brazing to form a hermetically sealed package. In certain instances, the metallic ring 212 may be a gold ring. Additional details about an exemplary coupling member 212 is described below in relation to FIG. 6.

Because the IMD 200 can be made into a hermetically sealed package via the joining of the header 202 to the housing 204, the feedthrough assembly typically arranged at the end portion of the housing 204 may not be needed, reducing the complexity of manufacturing the IMD 200 and allowing more space for the one or more components 206. For example, a feedthrough flange, feedthrough ports, electrodes, core clips and/or overmolding can be reduced and/or eliminated.

The illustrative IMD 200 shown in FIG. 2 is not intended to suggest any limitation as to the scope of use or functionality of embodiments of the subject matter disclosed throughout this disclosure. Neither should the illustrative IMD 200 be interpreted as having any dependency or requirement related to any single component or combination of components illustrated in FIG. 2. For example, in embodiments, the illustrative IMD 200 may include additional components. Additionally, any one or more of the components depicted in FIG. 2 can be, in embodiments, integrated with various ones of the other components depicted therein (and/or components not illustrated). Any number of other components or combinations of components can be integrated with the illustrative IMD 200 depicted in FIG. 2, all of which are considered to be within the ambit of this disclosure.

Figure 3:
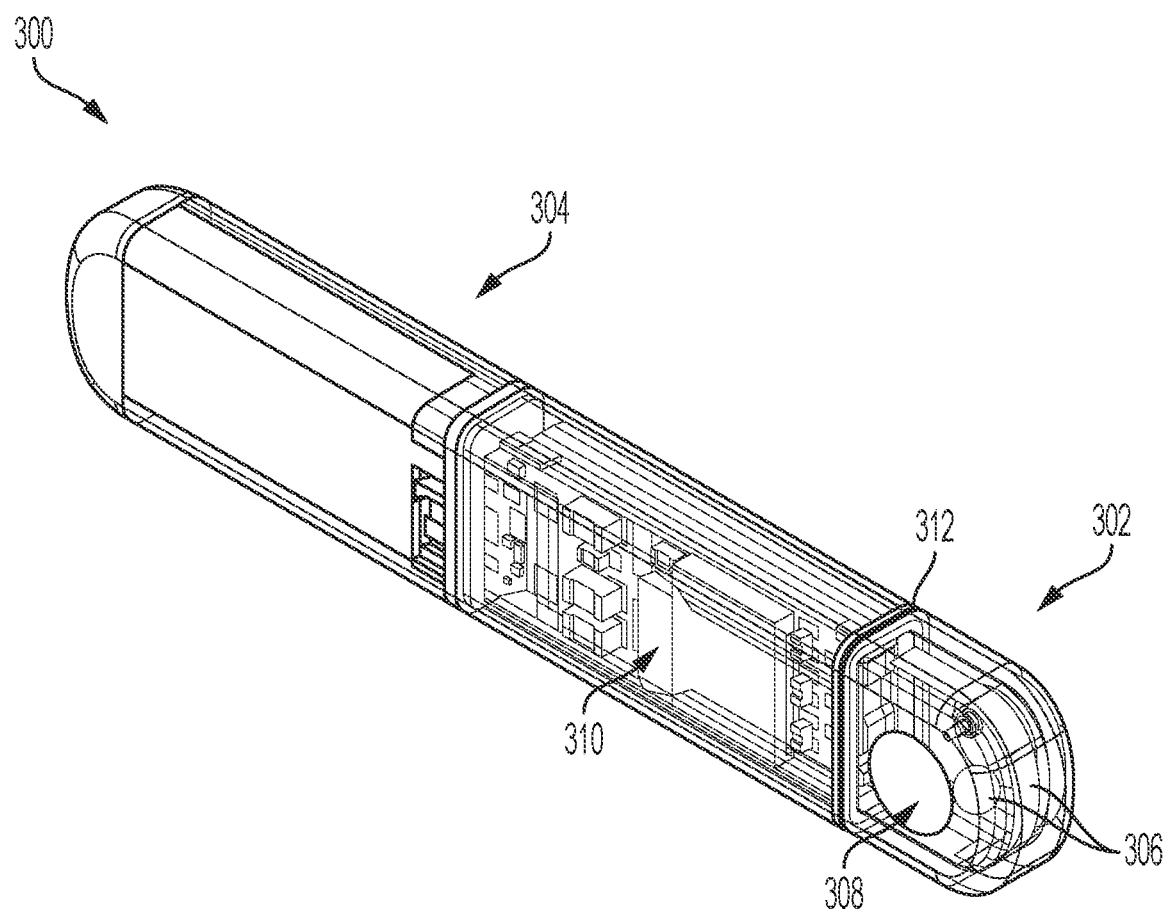
FIG. 3 is a perspective view of another IMD, in accordance with embodiments of the disclosure.

FIG. 3 is a perspective view of another IMD 300, in accordance with embodiments of the present disclosure. According to certain embodiments, the IMD 300 may be, or may be similar to, the IMD 102 depicted in FIG. 1 and/or the IMD 200 depicted in FIG. 2.

As shown, the IMD 300 may include a header 302 arranged at or near an end portion of the housing 304. In certain embodiments, the header 302 is formed from a non-conductive material. In certain instances, a non-conductive material may include materials having an electrical resistivity greater than $10^5$ Ω·m at 20° C. Examples of non-conductive materials include, but are not limited to, zirconia or alumina.

In certain embodiments, the header 302 defines a cavity (see, e.g., the cavity 412 of FIGS. 4-6). In some instances, the header 302 can be formed by, for example, injection molding or machining (e.g., milling) so the header 302 defines a cavity. As stated above, when a header is formed using an overmolding process, there is no cavity formed within the header. As such, headers formed using an overmolding process can result in wasted header space. Moreover, when a header is formed using an overmolding process, there can be yield fallout, resulting in additional costs associated with manufacturing the header. As such, the header 302 provides advantages over headers formed using an overmolding process.

According to some examples, one or more components 306 can be arranged within the cavity of the header 302. In certain instances, the one or more components 306 can be configured to and/or facilitate sensing physiological parameters, delivering therapy, and/or transmitting/receiving data. Examples of one or more components 206 include, but are not limited to, sensors, antennas, recharge coils, optical windows, electrical traces/connections, and/or the like. As explained in more detail below, the one or more components 306 arranged within the cavity of the header 302 may be supported by an internal surface of the cavity of the header 302. As mentioned above, due to the header 302 having a cavity, more space is available within the header 302 for components to be arranged therein.

According to certain embodiments, one or more electrodes 308 can be arranged on an outer surface of the header 302. In certain instances, the one or more electrodes 308 can be configured to and/or facilitate sensing physiological parameters and/or delivering therapy. In embodiments, the electrodes 308 can be coupled to one or more components 306 arranged within the header 302 through a conduit (illustrated in FIG. 6 below) in the header 302. In certain instances, the one or more electrodes 308 can be assembled/formed separate from the header 302 and then arranged on and/or coupled to a surface (e.g., an outer surface) of the header 302 by, for example, brazing the electrode 308 onto the surface of the header 302.

Additionally, or alternatively, the one or more components 306 and/or the one or more electrodes 308 can be coupled to internal components 310 arranged within the housing 304 of the IMD 300. According to certain embodiments, the internal components 310 may be used to control the one or more components 306 and/or the one or more electrodes 308.

According to certain embodiments, the header 302 can be coupled to and/or joined to the housing 304 via a coupling member 312 to form a hermetically sealed package. In certain examples, the coupling member 312 can be a metallic ring (e.g., titanium) that abuts, fits onto, and/or inserted into an open end of the header 302. In some examples, the coupling member 312 can be attached to the header 302 via brazing. And, the coupling member 312 can also be attached to the housing 304 via brazing to form a hermitically sealed package. In certain instances, the metallic ring 312 may be a gold ring. Additional details about an exemplary coupling member 312 is described below in relation to FIG. 6.

Because the IMD 300 can be made into a hermetically sealed package via the joining of the header 302 to the housing 304, the feedthrough assembly typically arranged at the end portion of the housing 304 may not be needed, reducing the complexity of manufacturing the IMD 300 and allowing more space for the one or more components 306.

The illustrative IMD 300 shown in FIG. 3 is not intended to suggest any limitation as to the scope of use or functionality of embodiments of the subject matter disclosed throughout this disclosure. Neither should the illustrative IMD 300 be interpreted as having any dependency or requirement related to any single component or combination of components illustrated in FIG. 3. For example, in embodiments, the illustrative IMD 300 may include additional components. Additionally, any one or more of the components depicted in FIG. 3 can be, in embodiments, integrated with various ones of the other components depicted therein (and/or components not illustrated). Any number of other components or combinations of components can be integrated with the illustrative IMD 300 depicted in FIG. 3, all of which are considered to be within the ambit of this disclosure.

FIG. 4 is a perspective view of an IMD 400 with a header 402 of the IMD 400 separated from a housing 404 of the IMD 400 and FIG. 5 is a perspective view of the header 402, in accordance with embodiments of the disclosure. According to certain embodiments, the IMD 400 may be, or may be similar to, the IMD 102 depicted in FIG. 1, the IMD 200 depicted in FIG. 2, and/or the IMD 300 depicted in FIG. 3.

In some examples, the housing 404 comprises an open end 406. According to certain embodiments, internal components 408 can be arranged within the housing 404 via the open end 406. Additionally, or alternatively, the housing 404 can comprise two halves and internal components 408 can be arranged within one or both halves of the housing 404. After which, the two halves can be fit together.

According to certain embodiments, the internal components 408 may be used to control one or more components 410 arranged within a cavity 412 of the header 402 and/or one or more electrodes 414 arranged on the header 402. Examples of one or more components 410 include, but are not limited to, sensors, antennas, recharge coils, optical windows, electrical traces/connections, and/or the like. In some instances, the header 402 can be formed by, for example, injection molding or machining (e.g., milling) so the header 402 defines the cavity 412. As stated above, when a header is formed using an overmolding process, there is no cavity formed within the header. As such, headers formed using an overmolding process can result in wasted header space. Moreover, when a header is formed using an overmolding process, there can be yield fallout, resulting in additional costs associated with manufacturing the header. As such, the header 402 provides advantages over headers formed using an overmolding process.

In some examples, the one or more electrodes 414 may be arranged on the header 402 by sputtering the electrode 414 onto the outer surface of the header 402. As another example, the one or more electrodes 414 may be arranged on the header 402 using photolithography to form the one or more electrodes 414 on the outer surface of the header 402. As even another example, the one or more electrodes 414 may be arranged on the header 402 by brazing the one or more electrodes 414 onto the outer surface of the header 402.

In certain embodiments, the open end 406 can comprise an end housing portion 416 configured to fit against a coupling member 418. In certain embodiments, the coupling member 418 is a metallic ring (e.g., titanium) that is fit against an end header portion 420 and secured to the end header portion 420 via brazing 422 (illustrated in FIG. 5). In some embodiments, the brazing 422 may be a brazed gold ring. In instances, the coupling member 418 may be integrated into the header 402. As such, the coupling member 418 and the header 402 may be collectively referred to herein as a header 402. Alternatively, the end housing portion 416 may fit against the end header portion 420 without a coupling member 418 in between.

In some examples, the end housing portion 416 can include a flange 424 that extends around the perimeter of the end housing portion 416. In some instances, the flange 424 may be formed to form a complementary fit with a flange 430 that extends around a perimeter of the coupling member 418 or the end header portion 420. In some instances, the flange 424 may be recessed with respect to an outer surface 426 of the housing 404. Additionally, or alternatively, the flange 424 may be recessed with respect to an inner surface 428 of the housing 404. In some instances, the flange 424 may be a thinned portion of a wall of the housing 404. In some embodiments, the flange 424 may be brazed to the coupling member 418 and/or the end housing portion 416 so the IMD 400 forms a hermetically sealed package.

In some examples, the coupling member 418 or an end header portion 420 can include a flange 430 that extends around the perimeter of the coupling member 418 or the end header portion 420, respectively. In some instances, the flange 430 may be recessed with respect to an outer surface 432 of the header 402 or an outer surface 434 (see FIG. 5) of the coupling member 418. Additionally, or alternatively, the flange 430 may be recessed with respect to an inner surface 436 (see FIG. 5) of the header 402 or an inner surface 438 (see FIG. 5) of the coupling member 418. In some instances, the flange 430 may be a thinned portion of a wall of the header 402 or a thinned portion of the coupling member 418. In some embodiments, the flange 430 is brazed to the end header portion 420 so the IMD 400 forms a hermetically sealed package.

In some examples, the flange 424 is configured to slide past the flange 430 when the housing 404 is brought together with the header 402. For example, when the header 402 and the housing 404 are brought together, the flange 424 is positioned adjacent to the flange 430 so that they at least partially overlap in an axial direction 440. In some instances, after the header 402 and the housing 404 are brought together, the housing 404 and the coupling member 418 and/or the header 402 are brazed together along the flanges 424, 430 so the IMD 400 forms a hermetically sealed package.

The illustrative IMD 400 shown in FIG. 4 and/or the header 402 shown in FIG. 5 is not intended to suggest any limitation as to the scope of use or functionality of embodiments of the subject matter disclosed throughout this disclosure. Neither should the illustrative IMD 400 and/or header 402 be interpreted as having any dependency or requirement related to any single component or combination of components illustrated in FIG. 4 or FIG. 5. For example, in embodiments, the illustrative IMD 400 and/or the header 402 may include additional components. Additionally, any one or more of the components depicted in FIG. 4 and/or FIG. 5 can be, in embodiments, integrated with various ones of the other components depicted therein (and/or components not illustrated). Any number of other components or combinations of components can be integrated with the illustrative IMD 400 depicted in FIG. 4 and/or the illustrative header 402 depicted in FIG. 5, all of which are considered to be within the ambit of this disclosure.

FIG. 6 is an exploded view of an illustrated header 502 of an IMD, in accordance with embodiments of the present disclosure. According to certain embodiments, the header 502 may be, or may be similar to, the header 202 depicted in FIG. 2, the header 302 depicted in FIG. 3, and/or the header 402 depicted in FIGS. 4-5. For example, the header 502 may be coupled to a housing of an IMD, such as the housing 110, the housing 204, the housing 304, and/or the housing 404.

As illustrated, the header 502 includes a cavity 504, an inner surface 506, an outer surface 508, a first side 510, and a second side 512 opposite the first side 510. In certain embodiments, the header 502 may be formed via machined (e.g., milled) and/or injection molded. In some instances, the header 502 can be formed by, for example, injection molding or machining (e.g., milling) so the header 502 defines the cavity 504. As stated above, when a header is formed using an overmolding process, there is no cavity formed within the header. As such, headers formed using an overmolding process can result in wasted header space. Moreover, when a header is formed using an overmolding process, there can be yield fallout, resulting in additional costs associated with manufacturing the header. As such, the header 502 provides advantages over headers formed using an overmolding process.

In certain embodiments, the header 502 may be formed from a non-conductive and/or dielectric material may include materials having an electrical resistivity greater than 105 Ω·m at 20° C. Examples of non-conductive materials include, but are not limited to, zirconia or alumina.

According to certain embodiments, one or more components 514 may be arranged within a cavity 504 of the header 502. Examples of the one or more components 514 include, but are not limited to, sensors, antennas, recharge coils, optical windows, electrical traces/connections, and/or the like. In certain instances, the one or more components 514 may be supported by the internal surface 506 of the cavity 504.

For example, the one or more components 514 may be an antenna 514 and the antenna 514 may be press fit into the cavity 504 and against an internal surface 506 of the cavity 504 so the internal surface 506 supports and affixes the antenna 514 in a fixed position. Because the one or more components 514 can be supported by the internal surface 506, a scaffolding assembly used to support internal components of a header may not be needed, reducing the complexity of manufacturing the header 502 and allowing more space for the one or more components 514. The antenna 514 may be formed a conductive material (e.g., gold) and may be, for example, equal to or less than 10 mils thick.

This positioning of the antenna 514 on an internal surface 506 of the cavity 504 may also provide the benefit of reducing corrosion that surrounding fluids could cause to the antenna 514. In certain instances, the antenna 514 is positioned equidistant from the first side 510 and the second side 512 of the header 502. Alternatively, the antenna 514 may be positioned closer to the first side 510 than the second side 512 or closer to the second side 512 than the first side 510. Because the header 502 is formed from a non-conductive and/or dielectric material in certain examples, the header 502 may provide less interference than other embodiments.

According to certain embodiments, the antenna 514 may be coupled to one or more components of the an IMD to which the header 502 is connected. For example, the antenna 514 may be coupled to internal components 210, 310, and/or 408 and may receive data from or transfer data to the one or more internal components 210, 310, and/or 408. Additionally, or alternatively, the antenna 514 may receive data from and/or transfer data to a receiving device external to the IMD to which the header 502 is coupled. For example, the antenna 514 may receive data from and/or transfer data to the receiving device 106.

In some examples, the header 502 includes one or more electrodes 516 arranged on an outer surface 508 of the header 502. In some examples, the one or more electrodes 516 may be arranged on the header 502 by sputtering the one or more electrodes 516 onto the outer surface of the header 502. As another example, the one or more electrodes 516 may be arranged on the header 502 using photolithography to form the one or more electrodes 516 on the outer surface of the header 502. As even another example, the one or more electrodes 516 may be arranged on the header 502 by brazing the one or more electrodes 516 onto the outer surface of the header 502.

In certain embodiments, the positioning of the one or more electrodes 516 on the outer surface 508 of the header 502 may reduce the header volume requirement and maximize the space within the header 502 for additional components to be incorporated. Additionally, or alternatively, the positioning of the electrode 516 on the outer surface 508 of a header 502 that is formed from a non-conducting and/or dielectric material may reduce impedance between the electrode 516 and the antenna 514.

To connect the electrode 516 to one or more components internal to the IMD to which the header 502 is coupled (e.g., internal components 210, 310, and/or 408), the header 502 may include one or more conduits 518 that extend through the header 502 (e.g., through the first side 510 and/or the second side 512). Further, a feedthrough 520 may extend through the conduit 518 of the header 502 and couple the electrode 516 to one or more components internal to the IMD to which the header 502 is coupled (e.g., internal components 210, 310, and/or 408). In some embodiments, the header 502 may include two or more feedthroughs 520. Further, the number of feedthroughs 520 may be equal to the number of conduits 518 and the number of electrodes 516 may equal the number of feedthroughs 520. In some instances, the diameters of the feedthroughs may be equal to or less than 20 mils in diameter.

To hermetically seal the header 502, the conduit 518 may be sealed hermetically with a preform ring 522. In certain instances, the preform ring 522 is formed from gold.

In some examples, the header 502 may include a coupling member 524. The coupling member 524 may be or be similar to the coupling member 212, 312, and/or 418. For example, the coupling member may be configured to be arranged at an end header portion 526. In certain embodiments, the coupling member 524 may include a flange 528 that extends around the perimeter of the coupling member 524. In some instances, the flange 528 may be formed to form a complementary fit with a flange on the end header portion 526. Additionally, or alternatively, the coupling member 524 may include a flange that is on an opposite side of the coupling member 524 to the flange 528. The flange on the opposite side of the coupling member 524 to the flange 528 may form a complementary fit to a flange included on an end housing portion (e.g., the flange 424).

In some instances, the flange 528 may be recessed with respect to an outer surface 530 of the coupling member 524. Additionally, or alternatively, the flange 528 may be recessed with respect to an inner surface 532 of the coupling member 524. In some instances, the flange 528 may be a thinned portion of the coupling member 524. In some embodiments, the coupling member is brazed to the end header portion 526 via a brazed ring 534 so the header 502 forms a hermetically sealed package once joined to a housing. In some instances, the brazed ring 534 may be gold.

The illustrative header 502 shown in FIG. 6 is not intended to suggest any limitation as to the scope of use or functionality of embodiments of the subject matter disclosed throughout this disclosure. Neither should the illustrative header 502 be interpreted as having any dependency or requirement related to any single component or combination of components illustrated in FIG. 6. For example, in embodiments, the illustrative header 502 may include additional components. Additionally, any one or more of the components depicted in FIG. 6 can be, in embodiments, integrated with various ones of the other components depicted therein (and/or components not illustrated). Any number of other components or combinations of components can be integrated with the illustrative header 502 depicted in FIG. 6, all of which are considered to be within the ambit of this disclosure.

Figure 7:
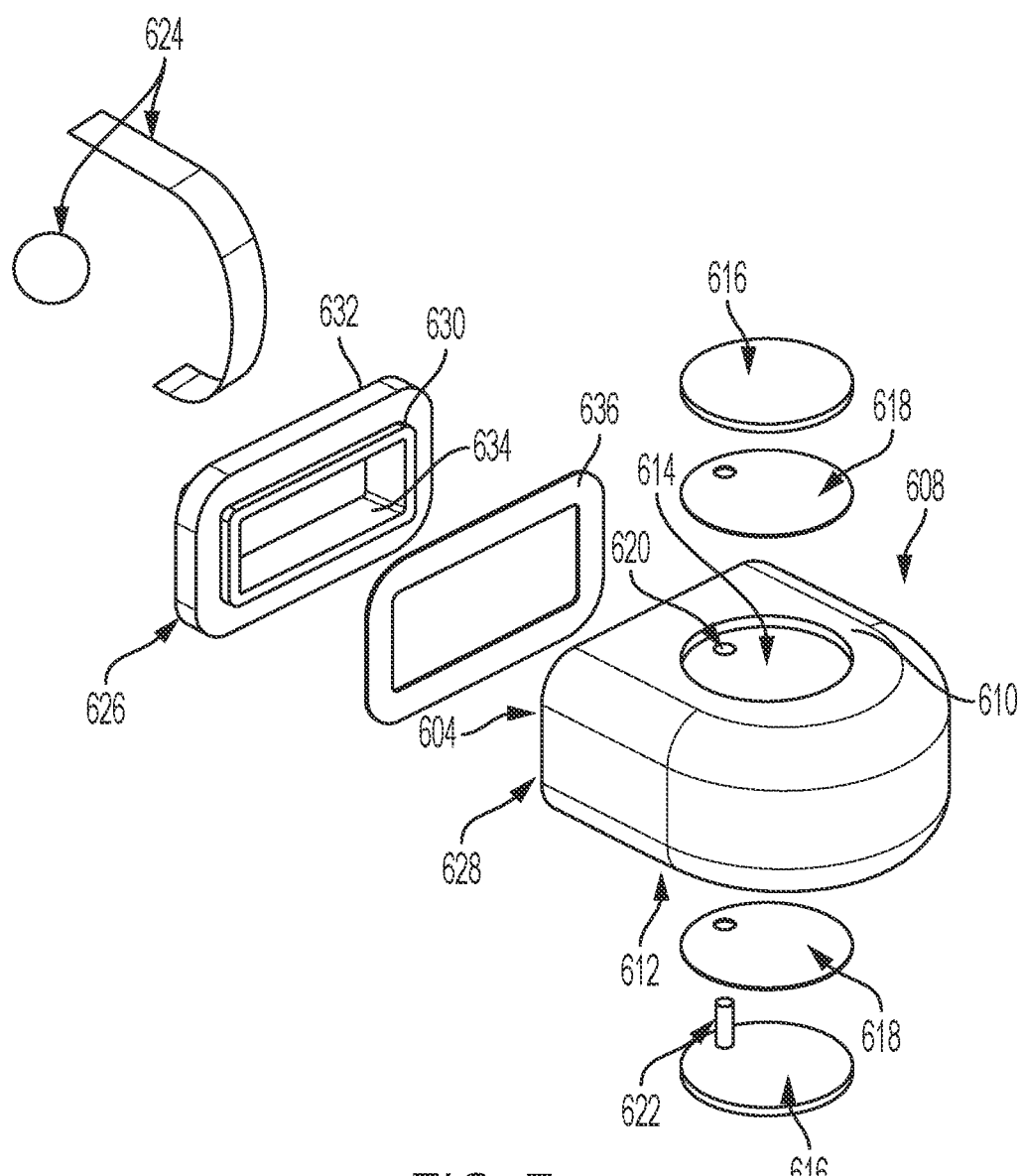
FIG. 7 is an exploded view of another header of an IMD, in accordance with embodiments of the disclosure.

FIG. 7 is an exploded view of an illustrated header 602 of an IMD, in accordance with embodiments of the present disclosure. According to certain embodiments, the header 602 may be, or may be similar to, the header 202 depicted in FIG. 2, the header 302 depicted in FIG. 3, the header 402 depicted in FIGS. 4-5, and/or the header 502 depicted in FIG. 6. For example, the header 602 may be coupled to a housing of an IMD, such as the housing 110, the housing 204, the housing 304, and/or the housing 404.

According to certain embodiments, the header 602 includes a cavity 604, an inner surface (not shown), an outer surface 608, a first side 610, and a second side 612 opposite the first side 610. In certain embodiments, the header 602 may be formed via machined (e.g., milled) and/or injection molded. In some instances, the header 602 can be formed by, for example, injection molding or machining (e.g., milling) so the header 602 defines the cavity 604. As stated above, when a header is formed using an overmolding process, there is no cavity formed within the header. As such, headers formed using an overmolding process can result in wasted header space. Moreover, when a header is formed using an overmolding process, there can be yield fallout, resulting in additional costs associated with manufacturing the header. As such, the header 602 provides advantages over headers formed using an overmolding process.

In certain embodiments, the header 602 may be formed from a non-conductive and/or dielectric material may include materials having an electrical resistivity greater than 105 Ω·m at 20° C. Examples of non-conductive materials include, but are not limited to, zirconia or alumina.

According to certain embodiments, the header 602 can include a recess 614 on an outer surface of the header 602, as illustrated. Within the recess 614, an electrode 616 may be disposed. In certain examples, the electrode(s) 616 can be shaped to fit within the recess 614 after the recess is defined. In some examples, the electrode(s) 616 may be arranged on the header 602 by sputtering the electrode(s) 616 within the recess 614. As another example, the electrode(s) 616 may be arranged on the header 602 using photolithography to form the electrode(s) 616 within the recess 614. As even another example, the electrode(s) 616 may be arranged on the header 502 by brazing the one or more electrode(s) 616 within the recess using, for example, an active braze alloy disc 618 for each of the one or more electrodes 616. In certain instances, the electrode(s) 616 can be formed from Ti with sputtered TiN. In certain instances, the braze alloy disc 618 may be formed from TiCuNi and have approximately 1-3 mils thickness.

In certain embodiments, the positioning of the one or more electrodes 616 on the outer surface 608 of the header 602 may reduce the header volume requirement and maximize the space within the header 602 for additional components to be incorporated. Additionally, or alternatively, the positioning of the electrode 616 on the outer surface 608 of a header 602 that is formed from a non-conducting and/or dielectric material may reduce impedance between the electrode 616 and the antenna 614.

To connect the electrode 616 to one or more components internal to the IMD to which the header 602 is coupled (e.g., internal components 210, 310, and/or 408), the header 502 may include one or more conduits 620 that extend through the header 602 (e.g., through the first side 610 and/or the second side 612). Further, a feedthrough 622 may extend through the conduit 620 of the header 602 and couple the electrode 616 to one or more components internal to the IMD to which the header 602 is coupled (e.g., internal components 210, 310, and/or 408). In certain embodiments, the feedthrough 622 may be part of the electrode 616 and in other embodiments, the feedthrough 622 may be a separate component than the electrode 616, but then is coupled to the electrode 616 by, for example, being brazed to the electrode 616. In some embodiments, the header 602 may include two or more feedthroughs 622. Further, the number of feedthroughs 622 may be equal to the number of conduits 620 and the number of electrodes 616 may equal the number of feedthroughs 622. In some instances, the diameters of the feedthroughs may be equal to or less than 20 mils in diameter.

To hermetically seal the header 602, the conduit 620 may be sealed hermetically by the braze alloy discs 618.

In certain examples, the recess 614 may be formed and/or defined via the injection molding of the header 602. According to certain embodiments, recesses 614 may be included on the first side 610 and/or the second side 612.

According to certain embodiments, one or more components 624 may be arranged within a cavity 604 of the header 602. Examples of the one or more components 624 include, but are not limited to, sensors, antennas, recharge coils, optical windows, electrical traces/connections, and/or the like. In certain instances, the one or more components 624 may be supported by the internal surface of the cavity 604.

For example, the one or more components 624 may be an antenna 624 and the antenna 624 may be press fit into the cavity 604 and against an internal surface of the cavity 604 so the internal surface supports and affixes the antenna 624 in a fixed position. Because the one or more components 624 can be supported by the internal surface, a scaffolding assembly used to support internal components of a header 602 may not be needed, reducing the complexity of manufacturing the header 602 and allowing more space for the one or more components 624. The antenna 624 may be formed a conductive material (e.g., gold) and may be, for example, equal to or less than 10 mils thick.

This positioning of the antenna 624 on an internal surface of the cavity 604 may also provide the benefit of reducing corrosion that surrounding fluids could cause to the antenna 624. In certain instances, the antenna 624 is positioned equidistant from the first side 610 and the second side 612 of the header 602. Alternatively, the antenna 624 may be positioned closer to the first side 610 than the second side 612 or closer to the second side 612 than the first side 610. Because the header 602 is formed from a non-conductive and/or dielectric material in certain examples, the header 602 may provide less interference than other embodiments.

According to certain embodiments, the antenna 624 may be coupled to one or more components of the an IMD to which the header 602 is connected. For example, the antenna 624 may be coupled to internal components 210, 310, and/or 408 and may receive data from or transfer data to the one or more internal components 210, 310, and/or 408. Additionally, or alternatively, the antenna 624 may receive data from and/or transfer data to a receiving device external to the IMD to which the header 602 is coupled. For example, the antenna 624 may receive data from and/or transfer data to the receiving device 106.

In some examples, the header 602 may include a coupling member 626. The coupling member 626 may be or be similar to the coupling member 212, 312, 418, and/or 524. For example, the coupling member 626 may be configured to be arranged at an end header portion 628. In certain embodiments, the coupling member 626 may include a flange 630 that extends around the perimeter of the coupling member 626. In some instances, the flange 630 may be formed to form a complementary fit with a flange on the end header portion 628. Additionally, or alternatively, the coupling member 626 may include a flange that is on an opposite side of the coupling member 626 to the flange 630. The flange on the opposite side of the coupling member 626 to the flange 630 may form a complementary fit to a flange included on an end housing portion (e.g., the flange 424).

In some instances, the flange 630 may be recessed with respect to an outer surface 632 of the coupling member 626. Additionally, or alternatively, the flange 630 may be recessed with respect to an inner surface 634 of the coupling member 626. In some instances, the flange 630 may be a thinned portion of the coupling member 626. In some embodiments, the coupling member 626 is brazed to the end header portion 628 via a brazed ring 636 so the header 602 forms a hermetically sealed package once joined to a housing. In some instances, the brazed ring 636 may be gold.

The illustrative header 602 shown in FIG. 7 is not intended to suggest any limitation as to the scope of use or functionality of embodiments of the subject matter disclosed throughout this disclosure. Neither should the illustrative header 602 be interpreted as having any dependency or requirement related to any single component or combination of components illustrated in FIG. 7. For example, in embodiments, the illustrative header 602 may include additional components. Additionally, any one or more of the components depicted in FIG. 7 can be, in embodiments, integrated with various ones of the other components depicted therein (and/or components not illustrated). Any number of other components or combinations of components can be integrated with the illustrative header 602 depicted in FIG. 7, all of which are considered to be within the ambit of this disclosure.

Figure 8:
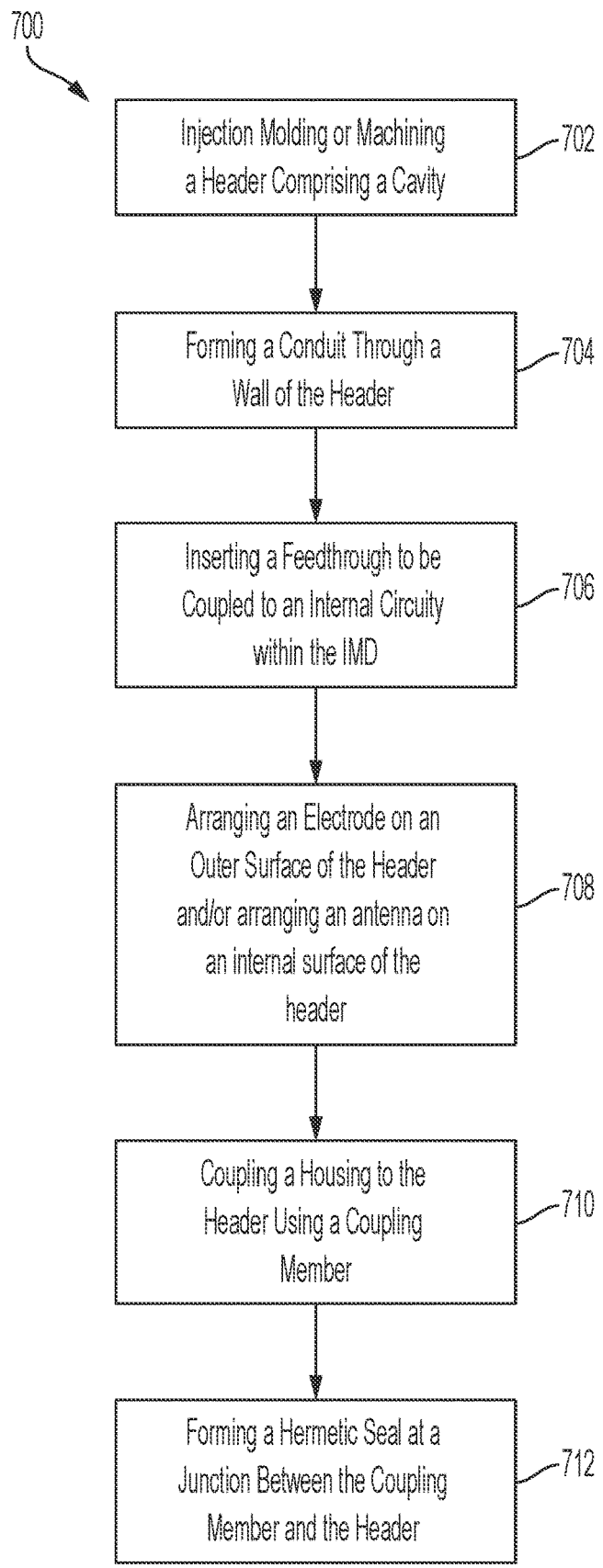
FIG. 8 is a flowchart illustrating a method of manufacture of an IMD, in accordance with embodiments of the disclosure.

FIG. 8 is a flowchart illustrating a method 700 of manufacturing of an IMD, in accordance with embodiments of the disclosure. In certain embodiments, the method 700 may include injection molding or machining (e.g., milling) a header comprising a cavity (block 702). In certain instances, the header may be, or be similar to the header 202, 302, 402, 502, and/or 602. For example, the header may be formed from a non-conductive material. In certain instances, the non-conducting material is zirconia or alumina. In certain instances, the header may include a recess, for example, the recess 614 illustrated in FIG. 7.

According to certain embodiments, the method 700 may include forming a conduit through a wall of the header (block 704). In some instances, the conduit may be or be similar to the conduit 518 illustrated in FIG. 6 or the conduit 620 illustrated in FIG. 7.

In certain examples, the method 700 may include inserting a feedthrough into the conduit such that the feedthrough may be coupled to the internal circuitry that is housed within the IMD (block 706). In certain instances, the feedthrough may be or be similar to the feedthrough 520 and/or the feedthrough 622. Additionally, or alternatively, the internal circuitry may be or be similar to the internal circuitry 210, 310, and/or 408.

According to certain embodiments, the method 700 includes arranging an electrode on an outer surface of the header that contacts the feedthrough (block 708). In certain examples, the electrode may be or be similar to the electrode 112, the one or more electrodes 208, the one or more electrodes 308, the one or more electrodes 414, the one or more electrodes 516, and/or the one or more electrodes 616. For example, arranging the electrode on the outer surface of the header may include sputtering the electrode onto the outer surface of the header. As another example, arranging the electrode on the outer surface of the header may include using photolithography to form the electrode on the outer surface of the header. As even another example, the step of arranging the electrode includes brazing the electrode onto the outer surface of the header.

Additionally, or alternatively, the method 700 may include arranging an antenna on an internal surface of the header (block 708). Arranging the antenna on an internal surface of the header may be or be similar to arranging the antenna 514 on an internal surface 506 of the header 502 and/or arranging the antenna 624 on an internal surface of the header 602. For example, the antenna may be press fit on an internal surface of the header. According to certain embodiments, the antenna may be equidistance from a first end and a second end of the header. In certain instances, the antenna may be formed from gold.

According to certain embodiments, the method 700 includes coupling a housing to the header using a coupling member (block 710). In certain examples, coupling the housing to the header may be or be similar to coupling the header 402 to the housing 404 as explained above. For example, a coupling member may be used to join the housing and the header. And, in certain instances, the coupling member may comprise opposing flanges that are each configured to be received either an end housing portion (e.g., the end housing portion 416 or an end header portion (e.g., the end header portion 420). For example, when the flange of the coupling member is received by the open end of the housing, the flange and the open end of the housing at least partially overlap along an axial direction of the IMD. In certain instances, the coupling member may be formed from titanium.

According to certain embodiments, the method 700 includes forming a hermetic seal at a junction between the coupling member and the header (block 712). In certain embodiments, forming the hermetic seal may include brazing a ring at the junction between the coupling member and the header, between the coupling member and the housing, and/or between the housing and the header.

In various embodiments, the method of forming an IMD may further comprise positioning an antenna within the cavity of the housing and pressing the antenna onto an internal surface of the housing so that the internal surface of the housing supports the antenna. In these embodiments, the antenna may be positioned equidistant from a first side and a second side of the header. Further, the antenna may be formed from gold.

The illustrative method 700 shown in FIG. 8 is not intended to suggest any limitation as to the scope of use or functionality of embodiments of the subject matter disclosed throughout this disclosure. Neither should the illustrative method 700 be interpreted as having any dependency or requirement related to any single block or combination of blocks illustrated in FIG. 8. For example, in embodiments, the illustrative method 700 may include additional blocks. Additionally, any one or more of the blocks depicted in FIG. 8 can be, in embodiments, integrated with various ones of the other blocks depicted therein (and/or blocks not illustrated). Any number of other blocks or combinations of blocks can be integrated with the illustrative method 700 depicted in FIG. 8, all of which are considered to be within the ambit of this disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. An implantable medical device (IMD), comprising:
   a housing comprising an open end;
   a header defining a cavity and comprising a conduit through a wall of the header, the header comprising a non-conductive material, the non-conductive material comprising a ceramic material;
   a coupling member comprising a flange, wherein the flange is configured to be received by the open end of the housing and wherein the flange and the open end of the housing at least partially overlap along an axial direction of the IMD when the flange is received by the open end;
   an electrode arranged on an outer surface of the header such that the electrode contacts and covers a portion of the ceramic material of the header;
   a feedthrough coupled to the electrode and extending through the conduit of the header, wherein the feedthrough is configured to be coupled to internal circuitry housed within the IMD; and
   a ring forming a hermetic seal between the coupling member and the header, wherein the ring is a metallic ring,
   wherein the IMD does not include a feedthrough assembly positioned at the open end when the IMD is fully assembled.

2. The IMD of claim 1, wherein the non-conductive material comprises zirconia.

3. The IMD of claim 1, wherein the ring comprises gold.

4. The IMD of claim 1, further comprising a recharge coil.

5. The IMD of claim 1, wherein the coupling member comprises titanium.

6. The IMD of claim 1, further comprising a braze coupling the electrode to the outer surface of the header.

7. The IMD of claim 1, further comprising a first braze coupling the coupling member to the header.

8. The IMD of claim 7, further comprising a second braze coupling the coupling member to the housing.

9. The IMD of claim 8, wherein the second braze is coupled to the flange.

10. The IMD of claim 1, wherein the feedthrough is a single conductive pin.

11. The IMD of claim 10, further comprising a preform ring arranged to surround the feedthrough.

12. The IMD of claim 11, wherein the preform ring comprises gold.

13. The IMD of claim 1, wherein the electrode is a first electrode, the IMD further comprising a second electrode positioned on an opposite side of the header from the first electrode.

14. The IMD of claim 1, wherein the header is not an overmolded header.

15. The IMD of claim 1, wherein the coupling member comprises a first material, wherein the ring comprises a second material, wherein the first material comprises titanium, wherein the second material comprises gold.

16. The IMD of claim 1, wherein the ring is formed to include only a single opening.

17. An implantable medical device (IMD), comprising:
   a housing comprising an open end;
   a header defining a cavity and comprising a conduit through a wall of the header, the header comprising a non-conductive material, the non-conductive material comprising a ceramic material;
   a coupling member comprising a flange, wherein the flange is configured to be received by the open end of the housing and wherein the flange and the open end of the housing at least partially overlap along an axial direction of the IMD when the flange is received by the open end;
   an electrode arranged on an outer surface of the header such that the electrode contacts and covers a portion of the ceramic material of the header;
   a feedthrough coupled to the electrode and extending through the conduit of the header,
   wherein the feedthrough is configured to be coupled to internal circuitry housed within the IMD; and
   a ring forming a hermetic seal between the coupling member and the header,
   wherein the IMD does not include a feedthrough assembly positioned at the open end when the IMD is fully assembled.

* * * * *